(12) United States Patent
Jadhav et al.

(10) Patent No.: US 12,213,963 B2
(45) Date of Patent: Feb. 4, 2025

(54) TOPICAL FORMULATION OF DISEASE-MODIFYING ANTIRHEUMATIC DRUG (DMARDS) FOR THE TREATMENT OF RHEUMATOID ARTHRITIS, MELANOMA, SQUAMOUS CELL CARCINOMA, ATOPIC DERMATITIS, AND PSORIASIS

(71) Applicant: Manoj Purushottam Jadhav, Hillsborough, NJ (US)

(72) Inventors: Manoj Purushottam Jadhav, Hillsborough, NJ (US); Mangal Shailesh Nagarsenkar, Thane (IN); Supriya Shrihari Shidhaye, Mumbai (IN); Shivali Hargovind Tank, Mumbain (IN); Bhagyashri Surendra Parab, Mumbai (IN); Pradnya Nikhil Korlekar, Mumbai (IN); Anita Pandurang Ayre, Mumbai (IN); Palak Karia, Mumbai (IN)

(73) Assignee: Manoj Jadhav, Hillsborough, NJ (US)

( * ) Notice: Subject to any disclaimer, the term of this patent is extended or adjusted under 35 U.S.C. 154(b) by 0 days.

(21) Appl. No.: 18/047,707

(22) Filed: Oct. 19, 2022

(65) Prior Publication Data
US 2024/0131008 A1 Apr. 25, 2024
US 2024/0226068 A9 Jul. 11, 2024

(51) Int. Cl.
| | |
|---|---|
| A61K 31/42 | (2006.01) |
| A61K 9/00 | (2006.01) |
| A61K 9/107 | (2006.01) |
| A61K 47/10 | (2017.01) |
| A61K 47/26 | (2006.01) |
| A61K 47/32 | (2006.01) |
| A61K 47/44 | (2017.01) |

(52) U.S. Cl.
CPC ............ *A61K 31/42* (2013.01); *A61K 9/0014* (2013.01); *A61K 9/1075* (2013.01); *A61K 47/10* (2013.01); *A61K 47/26* (2013.01); *A61K 47/32* (2013.01); *A61K 47/44* (2013.01)

(58) Field of Classification Search
CPC .... A61K 31/42; A61K 9/0014; A61K 9/1075; A61K 47/10; A61K 47/26; A61K 47/32; A61K 47/44
See application file for complete search history.

(56) References Cited

U.S. PATENT DOCUMENTS

2019/0247309 A1* 8/2019 Derrieu ................ A61K 31/365

FOREIGN PATENT DOCUMENTS

| CN | 103989675 A | 8/2014 | |
|---|---|---|---|
| EP | 2950796 A1 | 12/2015 | |
| IN | 2486MU2013 A | * 6/2015 | ............. A61K 38/17 |

OTHER PUBLICATIONS

Handbook of Pharmaceutical Excipients, 6th ed. Pharmaceutical Press, 2009: pp. 111-115, 535-538 and 580-584. (Year: 2009).*
Pund, S. et al. Transcutaneous delivery of leflunomide nanoemulgel: Mechanistic investigation into physicomechanical characteristics, in vitro anti-psoriatic and anti-melanoma activity. International Journal of Pharmaceutics, 2015. vol. 487 (1-2): 148-156. (Year: 2015).*
Souto, E.B. et al. Microemulsions and Nanoemulsions in Skin Drug Delivery. Bioengineering (Basel), 2022. vol. 9, No. 158. Published Apr. 5, 2022 (Year: 2022).*
ABITEC Corporation. "Capmul® multi-functional lipids", webpage, Jun. 12, 2020. Retrieved from Internet Archive Wayback Machine <https://web.archive.org/web/20200612052413/https://www.abiteccorp.com/en/product-repository/capmul-multi-functional-lipids/> on May 15, 2024. (Year: 2020).*
Porter, M. R. Handbook of Surfactants, 1st edition. Boston, MA: Springer US, 2991. Web. (Year: 1991).*
Yang, S. G. et al. Stable bioavailability of cyclosporin A, regardless of food intake, from soft gelatin capsules containing a new self-nanoemulsifying formulation. International journal of clinical pharmacology and therapeutics, 2006. vol. 44(5). [abstract]. (Year: 2006).*
Mona A. Shewaiter et al., Formulation and characterization of leflunomide/diclofenac sodium microemulsion base-gel for the transdermal treatment of inflammatory joint disease. Journal of Drug Delivery Science and Technology, available online Oct. 1, 2020. https://doi.org/10.1016/j.jddst.2020.102110.
Vivek Verma and T.S. Easwari, A novel approach of leflunomide nanoemulgel for topical drug delivery system. International Journal of Pharmaceutical Investigation, 2022; 12(2) Apr.-Jun.: pp. 199-204. DOI: 10.5530/ijpi.2022.2.35.
Vivek Verma and T.S. Easwari, Anti-inflammatory effect of disease-modifying anti-rheumatic drug, leflunomide: A Review. International Journal of Pharmaceutical Sciences and Research, vol. 13(7): pp. 2648-2654, published online Jul. 1, 2022. http://dx.doi.org/10.13040/IJPSR.0975-8232.13(7).2648-54.

(Continued)

*Primary Examiner* — Amy L Clark
*Assistant Examiner* — Chihyi Lee
(74) *Attorney, Agent, or Firm* — Transformative Legal LLC; Len S. Smith (57) ABSTRACT

The present invention relates to a composition of disease-modifying antirheumatic drugs (DMARDs) for treatment of auto-immune diseases. More particularly, the invention relates to the microemulsion based emulgel composition of DMARD-leflunomide or its derivatives for treatment of auto-immune diseases such as rheumatoid arthritis, atopic dermatitis, psoriasis and skin cancer such as melanoma, squamous cell carcinoma. The invention also discloses a method for preparation of microemulsion based emulgel composition with improved physicochemical, pharmacokinetic properties of leflunomide to be used in pharmaceutical compositions. This invention discloses the delivery of leflunomide across human skin for the treatment of autoimmune and oncological conditions. The unique delivery of leflunomide in the form of microemulsion based emulgel composition is disclosed.

4 Claims, 4 Drawing Sheets

(56) References Cited

OTHER PUBLICATIONS

Examination report under sections 12 & 13 of the Patents Act, 1970, Government of India, for Application No. 202221059797, dated Apr. 18, 2023.
Bae et al. "Topical delivery of leflunomide for rheumatoid arthritis treatment: evaluation of local tissue deposition of teriflunomide and its anti-inflammatory effects in an arthritis rat model." Drug Dev Ind Pharm 2016;42(2):254-62. Epub May 26, 2015.
Hearing Notice on Dec. 19, 2023 for India Patent Application 202221059797.
Amendments to the Claims on Jul. 17, 2023 for India Patent Application 202221059797.
Response to the First Examination Report on Jul. 17, 2023 for India Patent Application 202221059797.
Response to Hearing. Written Submission on Jan. 25, 2024 for India Patent Application 202221059797.
Zhang et al. "Design and evaluation of a novel transdermal patch containing diclofenac and teriflunomide for rheumatoid arthritis therapy." Asian J Pharm Sci Oct. 2014; vol. 9, Issue 5, pp. 251-259. Epub Aug. 27, 2014. doi: 10.1016/j.ajps.2014.07.007.

* cited by examiner

Figure 1a: Concentration versus time profile for low dose topical formulation in pharmacokinetic study Figure 1b: Concentration versus time profile for high dose topical formulation in pharmacokinetic study Figure 1c: Concentration versus time profile for oral dose formulation in pharmacokinetic study

Figure 2: Comparative concentration versus time profile for a: Low dose topical; b: High dose topical; c: Oral dose in pharmacokinetic study

TOPICAL FORMULATION OF DISEASE-MODIFYING ANTIRHEUMATIC DRUG (DMARDS) FOR THE TREATMENT OF RHEUMATOID ARTHRITIS, MELANOMA, SQUAMOUS CELL CARCINOMA, ATOPIC DERMATITIS, AND PSORIASIS

TECHNICAL FIELD OF THE INVENTION

The present invention relates to a composition of disease-modifying antirheumatic drugs (DMARDs) for treatment of auto-immune diseases. More particularly, the invention relates to the microemulsion based emulgel composition of DMARD-leflunomide or its derivatives for treatment of auto-immune diseases such as rheumatoid arthritis, atopic dermatitis, psoriasis and skin cancer such as melanoma, squamous cell carcinoma and uveitis. The invention also discloses a method for preparation of microemulsion based emulgel composition with improved solubility pharmacokinetic properties of leflunomide to be used in pharmaceutical compositions. This invention discloses the delivery of leflunomide across human skin for the treatment of autoimmune and oncological conditions. The unique delivery of leflunomide in the form of microemulsion based emulgel composition is disclosed. The topical delivery provides several advantages like localized delivery of drugs, reduced drug exposure, ease of administration and improved patient compliance.

BACKGROUND OF THE INVENTION

Rheumatoid arthritis (RA) is an autoimmune disease that causes joint pain and damage throughout the human body. Rheumatoid arthritis mainly attacks the joints, usually many joints at once. The joint damage occurs at both sides of the body e.g., right and left knee, wrist etc. Rheumatoid arthritis is a common systemic inflammatory autoimmune disease characterized by painful, swollen joints that severely impairs physical function and quality of life.

Rheumatoid arthritis is caused when the immune system is not working properly thus causing joint inflammation and pain. Approximately 70% of rheumatoid arthritis patients have a chronic course and 15% of them generally develops a severe, progressive, crippling form of arthritis. It mainly affects the joints in hands, knees and wrists. Typically, in rheumatoid arthritis, the lining of the joint gets inflamed, causing damage to the joint tissues. Rheumatoid arthritis also affects the other tissues throughout the body and cause problems in the lungs, circulatory system and eyes.

Rheumatoid arthritis usually develops during middle age and twice as often in females than males. In the early stages, patients with rheumatoid arthritis may not see redness or swelling in the joints, but they may experience tenderness and pain. However, the symptoms include joint pain, tenderness, swelling or stiffness that lasts for six weeks or longer, and morning stiffness. In addition, many people with rheumatoid arthritis also suffer from fatigue and low-grade fever.

Rheumatoid arthritis is diagnosed by examining a blood test result, examining the joints and organs, and reviewing x-ray or ultrasound and by assessment of symptoms, and physical examination. The diagnosis is based on holistic assessments and combination of all physical examination, lab tests and clinician's judgement.

The treatment modalities for rheumatoid arthritis have improved greatly in the past 30 years. Current treatments give most patients good relief of symptoms and keep them functioning at, or near, normal levels. With the right medications, many patients can have no signs of active disease. When the symptoms are completely controlled, the disease is in "remission".

Even though there is no cure for rheumatoid arthritis, the goal of treatment is to reduce the joint pain and swelling, and to improve the ability to perform day-to-day activities. The initiation of medication at the earliest phase helps prevent the joints from having lasting or possibly permanent damage. However, no single treatment works for all the patients. Many people with rheumatoid arthritis must change their treatment at least once during their lifetime.

It is observed that the typical standard of care includes the treatment with pain medications, anti-inflammatory drugs, corticosteroids, etc. There also is a class of drugs which helps to slow the damage to the joints and the cartilages in the patients. These are termed disease-modifying antirheumatic drugs (DMARDs) that act by blocking the body's immune system and delays the disease progression of rheumatoid arthritis.

In addition, biologics such as adalimumab, abatacept, adalimumab-adbm etc. are also a recent new intervention as they provide a targeted response to the inflammation rather than blocking the entire immune system of the body. These drugs are also an effective treatment option to the patients who do not respond to the DMARDs. Further, a novel class of drugs called janus kinase inhibitors such as baricitinib, tofacitinib, upadacitinib are effective to treat the inflammation and inhibit damage to the joints where other two options don't respond.

Among the DMARDs, prominent drugs that are widely used are methotrexate, leflunomide, hydroxychloroquine, sulfasalazine, brequinar sodium, etc. and these drugs are approved as first line treatment options for the rheumatoid arthritis. In addition, other drugs that can be further investigated includes raltegravir and acalabrutinib, which has been investigated in silico for human dihydroorotate dehydrogenase (DHODH) inhibition activity.

Leflunomide is a pyrimidine synthesis inhibitor and immunosuppressive disease-modifying antirheumatic drug used in active moderate-to-severe rheumatoid arthritis and psoriatic arthritis. Leflunomide is a US-FDA approved drug indicated for the treatment of rheumatoid arthritis (Arava® tablets, 10 mg, 20 mg, 100 mg). Leflunomide is an isoxazole, which is metabolized into an active metabolite melononitrilamide i.e. A771726. Upon conversion to its metabolite, leflunomide exerts immunomodulatory action to treat rheumatoid arthritis by inhibiting dihydroorotate dehydrogenase (DHODH), a rate limiting enzyme of the de novo pyrimidine synthesis pathway. Dihydroorotate dehydrogenase is a flavin-dependent mitochondrial enzyme that catalyzes fourth reaction of pyrimidine de-novo synthesis. It also exhibits an anti-inflammatory effect. However, the long-term use in the treatment of rheumatoid arthritis exhibits some side effects when given in the available dosage form i.e., oral tablets (10, 20 and 100 mg). The known side effects are embryo fetal toxicity in animals and hepatotoxicity in humans. Leflunomide carries a black box warning due to these side effect. Other general adverse effects are diarrhea, respiratory infections, nausea, headache, rash, abnormal liver enzymes and dyspepsia.

The dosing regimen of leflunomide include a loading dose of 100 mg for 3 days, followed by maintenance dose of 20 mg daily. The dose can be adjusted to 10 mg if the higher dose is not tolerated. Considering the long-term nature of this lifestyle disease, there exists a need to find novel strategies and innovative approaches to reduce the drug exposure to these immunocompromised patients. The mode of administration of drug using a suitable formulation plays an important role in the efficacy of the drug. If the suitable mode is not selected, most of active ingredient shall be lost in the blood stream before reaching the site of action and therefore may also require a higher dose.

Chinese Patent Application No. CN103989675A entitled "Leflunomide tablet and preparation technology thereof" discloses leflunomide tablets, a preparation technology and use thereof. The product is prepared from leflunomide, milk sugar (i.e., lactose), pregelatinized starch, hydroxypropyl methyl cellulose, carboxymethyl starch sodium, polysorbate-80, 12% slushing pregelatinized starch, magnesium stearate and a gastric soluble film coating premix. The production method comprises the steps of fabricating tablets and coatings, and the like. The leflunomide tablet disclosed in the application is characterized as being high in dissolution rate, good in stability, good in anti-inflammatory analgesic effect, and small in effect on erythrocyte sedimentation rate, and the total effective rate is 85%. The drug disclosed in the application is characterized as having the characteristics of being fewer in medication administration times, stable in plasma concentration, long in lasting time and the like.

European patent application No. EP2950796A1 entitled "Pharmaceutical composition comprising leflunomide" discloses a pharmaceutical composition comprising leflunomide, which is prepared as a single dose of 14 to 17.5 mg. The application discloses the use of leflunomide for the prophylaxis and/or treatment of autoimmune disease, preferably rheumatoid arthritis, psoriatic arthritis, cystic fibrosis complication of cystic fibrosis, lupus nephritis, systemic lupus erythematosus, uveitis, myasthenia gravis and/or of granulomatosis with polyangitis (Wegener's disease); and/or in the context of organ transplantation prophylaxis and/or treatment, preferably kidney transplantation and/or liver transplantation; and/or in the prophylaxis and/or treatment of oncological diseases, preferably melanomas, sarcomas, gliomas, prostate carcinomas, brain and/or CNS tumors; and/or in the prophylaxis and/or treatment of diseases with the human immunodeficiency virus (HIV).

The Publication entitled *"Topical delivery of leflunomide for rheumatoid arthritis treatment: evaluation of local tissue deposition of teriflunomide and its anti-inflammatory effects in an arthritis rat model"* by Joonho Bae et al., Drug Dev. Ind. Pharm, 2016, 42 (2): 254-62. discloses topical delivery of leflunomide and teriflunomide, its active metabolite, its local tissue deposition and its assessment of anti-inflammatory effects in a rat model. They disclose that leflunomide can be delivered topically and metabolized into teriflunomide through the rat skin and evaluated the therapeutic effect of topical leflunomide. It is concluded that topical delivery of leflunomide across animal skin and in turn teriflunomide was effective in arthritic joint which can provide better compliance, less side effects in rheumatoid arthritis patients.

The Publication entitled *"Design and evaluation of a novel transdermal patch containing diclofenac and teriflunomide for rheumatoid arthritis therapy"* by Zhang et al., Asian Journal of Pharmaceutical Sciences, Vol. 9, Issue 5, October 2014, pages 251-259, discloses the development of a transdermal patch containing diclofenac and teriflunomide for the treatment of rheumatoid arthritis. The publication assessed the effect of various organic amine salts of diclofenac sodium and their forming was assessed using differential scanning calorimetry (DSC) and FTIR. It is observed that teriflunomide-triethylamine (TEF-TEtA) enhanced the skin permeation of teriflunomide. Hence, the use of triethylamine salt was described as being beneficial for the transdermal permeation of teriflunomide and diclofenac sodium both in-vitro and in-vivo.

The publication *"A Novel Approach of Leflunomide Nanoemulgel for Topical Drug Delivery System"* by Vivek Verma et al, Int. J. Pharm. Investigation, 2022; 12 (2): 199-204 discloses nanoemulgel for topical delivery of leflunomide.

Leflunomide has the required efficacy; however, it has safety concerns considering the long term use in the patients. Among several considerations to improve the safety profile (e.g. hepatotoxicity, fetal toxicity) while maintaining the efficacy are to improve/modify the route of delivery of the DMARDs including leflunomide, reduce drug exposure with an aim to minimize adverse effects, and develop scalable, reproducible formulations from viable commercial perspective.

Hence, in order to overcome the disadvantages that exist in the state of the art, there is need for an improved formulation along with an effective mode of delivery for improved efficacy in human.

The inventors of present invention have developed a topical microemulsion based emulgel composition comprising,
a. Leflunomide;
b. Combination of surfactants; and
c. Pharmaceutically acceptable inert excipients.

DETAILED DESCRIPTION OF THE INVENTION

In order to more clearly and concisely describe and point out the subject matter of the claimed invention, the following definitions are provided for specific terms, which are used in the following written description.

The term "disease-modifying antirheumatic drugs (DMARDs)" refers to a class of drugs which do not cure the disease but prevent it from worsening.

The term "topical delivery" refers to a process in which a formulation is applied on the skin for local or systemic action.

By the term "autoimmune disease" (synonymous with "autoimmune disorder"), it is meant to any condition or disease related to immune system such as rheumatoid arthritis, multiple sclerosis, Type I diabetes mellitus, psoriasis, psoriatic arthritis and ankylosing spondylitis. In a preferred embodiment, the autoimmune disease is rheumatoid arthritis, multiple sclerosis or psoriasis.

The term "effective amount" or "therapeutically effective amount" refers to the amount of an active agent sufficient to induce a desired biological result. That result may be alleviation of the signs, symptoms, or causes of a disease, or any other desired alteration of a biological system. The term "therapeutically effective amount" is used herein to denote any amount of the formulation which causes improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

As used herein, "treatment" or "treating," or "ameliorating" are used interchangeably. These terms refer to an approach for obtaining beneficial or desired results including but not limited to a therapeutic benefit and/or a prophylactic benefit. Therapeutic benefit is meant to indicate eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

A "subject," "individual," or "patient," is used interchangeably herein, which refers to a vertebrate, preferably a mammal, more preferably a human. Tissues, cells and their progeny of a biological entity obtained in vitro or cultured in vitro are also encompassed.

The use of the terms "a" and "an" and "the" and similar referents in the context of describing the elements (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential to the practice of the invention.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The present invention discloses a composition of disease-modifying antirheumatic drugs (DMARDs) for treatment of auto-immune diseases. The composition of the present invention comprises leflunomide as active ingredient for topical or transdermal delivery for treatment of auto-immune diseases such as rheumatoid arthritis, atopic dermatitis, psoriasis and skin cancers such as melanoma, squamous cell carcinoma. The invention also discloses a method for preparation of microemulgel with improved physicochemical and pharmacokinetic properties of leflunomide to be used in pharmaceutical compositions.

The composition of the present invention is prepared in the form of a microemulsion based gel. An emulgel is a semisolid topical drug delivery system which has gained interest due to its dual release control nature i.e. emulsion and gel. Emulsions are controlled release systems containing two immiscible phases in which one internal phase is dispersed into the other external phase with the use of an emulsifying agent to stabilize the system. Emulsion are of two types; oil-in-water or water-in-oil, where the drug molecule trapped in internal phase passes through the external phase and is gradually permeated into the skin to give improved impact. Gels have been consistently used in topical or transdermal drug delivery systems. It is a semisolid formulation which shows the external solvent phase, is hydrophilic or hydrophobic in nature and is immobilized within the spaces available of a three-dimensional network structure. Gels are elastic and rigid in nature. They have a wide range of application in food technologies, cosmetics and medicines.

Emulsion and gel when developed in combination is referred to as emulgel. The main objective of emulgel is to deliver hydrophobic drug molecule through skin. Gels have good loading capacity due to vast network of interconnecting pores. Emulgel are being developed to treat various skin disorders. Emulgel preparation includes simple and small steps which had ability to have enhance production at large scale. They are easy to apply and are relatively less greasy. Emulgels offer more stability due to increased viscosity of the aqueous phase. For drugs with less water solubility, emulgel forms a good alternative. It has also proven to be a stable vehicle for hydrophobic drugs.

Emulgels are either emulsion of water in oil or oil in water type, which gets gelled by mixing it with a gelling agent. Emulsion incorporation into gel enhances stability. Due to insoluble excipients and lack of excess oil base makes better drug release than other topical formulations. Nonetheless, various challenges exist in formulating an ideal emulgel formulation that is free from causing irritation at the site of application and that has the potential to readily cross the barrier of the layers of skin. Added to these limitations, drug delivery across the layers of skin is cumbersome in subjects with different fungal infections. The inventors have recognized that there is a need for improved emulgel formulations that have the potential to alleviate the limitations of irritation and crossing the layers of skin and still provide efficacy.

In an embodiment, the presentation a topical microemulsion based emulgel composition comprising,
a. Leflunomide;
b. Combination of surfactants; and
c. Pharmaceutically acceptable inert excipients.

"Surfactants" are integral components of an emulsion system which is used to stabilize the thermodynamically unstable mixture of two immiscible liquids by reducing the interfacial tension between them and change the dispersion entropy. Safety, stability and high drug loading capacity along with good emulsification properties are the basic requirements for the surfactants integrated in emulsion development. A suitable surfactant used in emulsion formulation should be adsorbed rapidly onto the interface of the two immiscible phases leading to reduction of interfacial tension and prevents coalescence of the droplets. Commonly used commercially available surfactants used in the emulgel and emulsion system include Kolliphor® RH 40, Capryol® 90, Labrafil® CS, Labrasol®, Gelucire® 44/14, Gelucire® 50/13, Cremophor® RH 40, Cremophor® EL, Imwitor® 491, Imwitor® 742, Imwitor® 780 K, Imwitor® 928, Imwitor® 988 M, Imwitor® 2125 CS, Lauroglycol™ 90, PEG MW>4000 (polyethylene glycol greater than 4,000 Daltons), Plurol® Oleique CC 497, poloxamer 124, poloxamer 188, Softigen® 701, Softigen® 767, Tween® 20, Tween® 60, and Tween® 80.

Capryol® 90 is also known as propylene glycol monocaprylate NF and propylene glycol caprylate, and these names are used interchangeably herein.

Capmul® PG2L is also known as propylene glycol dilaurate, and these names are used interchangeably herein.

Tween® 20, also known as polysorbate 20, is polyoxyethylene sorbitol ester that belongs to the polysorbate family and these names are used interchangeably herein.

Carbopol® 974P is also known as carbomer and carboxypolymethylene and these names are used interchangeably herein.

Kolliphor® RH 40 is a nonionic solubilizer and emulsifying agent obtained by reacting 40 moles of ethylene oxide with 1 mole of hydrogenated castor oil. The main constituent of Kolliphor® RH 40 is glycerol polyethylene glycol ("PEG") oxystearate, which, together with fatty acid glycerol polyglycol esters, forms the hydrophobic part of the product. The hydrophilic part consists of polyethylene glycols and glycerol ethoxylate. Kolliphor® RH 40 is a white to yellowish paste at 20° C. Synonyms for Kolliphor® RH 40 include Cremophor® RH 40, macrogolglycerol hydroxystearate, PEG-40 castor oil, and polyoxyl 40 hydrogenated castor oil and these names are used interchangeably herein.

In an aspect of one embodiment, the combination of surfactants includes polysorbate 20, polyoxyl 40 hydrogenated castor oil and polyethylene glycol MW>4,000 (molecular weight greater than 4,000 Daltons). In another aspect of one embodiment, the surfactants include polysorbate 20 and polyoxyl 40 hydrogenated castor oil in a weight ratio of 1:1.

"Co-surfactants" are those that help surfactant(s) in the emulsion system to emulsify oil in the aqueous phase. In such a system, the co-surfactant mixes with the surfactant and penetrates into the surfactant layer, thereby disrupting the interfacial film, lowering the interfacial tension, and helping with the emulsification process. Usually transient negative interfacial tension and fluid interfacial film cannot be achieved by using surfactant only, so incorporation of a co-surfactant provides flexibility to the interfacial film. Co-surfactants may also help in solubilization of the oil by modification of the interface of the oil-water. Selection of a co-surfactant is important because release of the therapeutic agent or lipophilic drugs is affected by its partitioning in aqueous and oil phase by interaction between surfactant and co surfactant. Transcutol® HP, 1,2-propylene glycol, PEG-400, carbitol, absolute ethyl alcohol, propanol and butanol are used frequently as co-surfactants in emulgel and emulsion system.

Leflunomide is poorly soluble making it difficult to formulate and achieve absorption through the skin when administered as a topical dosage form. The inventors of the present invention surprisingly found that a specific combination of surfactants mixed together with an oil provides a combination that gives a stable microemulsion with satisfactory globule size and in turn helps achieve improved absorption through the skin. The relevant data is included in Example 1 below.

The pharmaceutically acceptable inert excipients as per the invention include oil, gelling agents and solvents.

"Gelling Agents" are the polymers essential to give the structural network for the preparation of gels. The gelling agents can be natural, semisyntheric or synthetic. Natural gelling agents include agar, tragacanth, guar gum, and xantham gum. Semisynthetic and synthetic gelling agents include carbopol, HPMC (cellulose derivatives) and poloxamer.

Commercially available grades of carbopol like Carbopol® 974P can be used. Carbopol® 974P NF polymer is highly crosslinked and produces highly viscous gels with short flow. Carbopol® 974P NF is an oral pharmaceutical grade of carbomers. It readily hydrates, absorbs water, and swells. These properties make it a potential candidate for use in topical dosage forms.

The present invention discloses the development of the dermatologically suitable dosage form of leflunomide for the treatment of rheumatoid arthritis, melanoma, psoriasis or atopic dermatitis and squamous cell carcinoma.

The foregoing examples are illustrative embodiments and are merely exemplary. A person skilled in the art may make variations and modifications without deviating from the spirit and scope of the invention. All such modifications and variations are intended to be included within the scope of the claims.

Example 1—Leflunomide Solubility Studies

Solubility of leflunomide was investigated in various oils, surfactants and co-surfactants. The selected excipients showing good solubility were further screened using turbidimetric method to check the emulsification efficiency of the system. Water titration method was used to select combination of oil, surfactant and co surfactant which provided clear systems with water. Briefly, the drug was dissolved in the oil by vortexing. Surfactant and co-surfactants were added to the oil phase and further titrated with water to check the ease of emulsification. The globule size of these systems was determined.

Based on the solubility studies, emulsification studies and results of globule size distribution, the following combinations of oil, surfactant and co-surfactants were selected:

Based on the solubility studies and emulsification of leflunomide in various oils, Capryol® 90, Kollisolv® MCT and Capmul® PG2L were selected for formulation development.

TABLE 1

Solubility studies of Leflunomide in various oils and surfactants

| | Oil | Surfactant | Co-Surfactant | Particle Size | Polydispersity index | Appearance |
|---|---|---|---|---|---|---|
| 1. | Capmul ® PG2L | Tween ® 20 | PEG 400 | 180.2 | 0.531 | Transparent |
| 2. | Capmul ® PG2L | Kolliphor ® RH 40 | PEG 400 | 251.6 | 0.359 | Slightly opalescent |
| 3. | Capryol ® 90 | Tween ® 20 | PEG 400 | 234.6 | 0.412 | Transparent |
| 4. | Capryol ® 90 | Kolliphor ® RH 40 | PEG 400 | 263.8 | 0.435 | Slightly opalescent |
| 5. | Kollisolv ® | Labrasol ® | Acconon ® AKG 6 | 680.2 | 0.291 | Phase separation |
| 6. | Kollisolv ® | Labrasol ® | PEG 400 | 1009.5 | 0.392 | Phase separation |

The emulsions formed using Capmul® PG2L and Capryol® 90 with Tween® 20 gave globule size below 500 nm. Kollisolv® MCT resulted in a globule size in a higher range with phase separation on standing, and therefore was unacceptable under the conditions used.

Capryol® 90 and Capmul® PG2L were selected as the oil component. The solubility of the drug was highest in these oils and adequate to achieve the required drug loading. The surfactants selected were Tween® 20 and Kolliphor® RH 40 as these compounds showed high drug solubility and greater emulsification properties with the selected oils. PEG 400 was selected as the co-surfactant as it had higher drug solubility, imparting homogeneity to the system and contributing to achieve an emulsion with less globule size with good stability. Out of the various gelling agents screened, Carbopol® 974P was selected because it formed uniform gel with good texture and consistency.

Example 2—Leflunomide Microemulsion Compositions According to the Invention

TABLE 2a

Formulation composition and characterization of batches ME1 to ME9 of microemulsion

| SN | Composition (w/v %) | ME1 | ME2 | ME3 | ME4 | ME5 | ME6 | ME7 | ME8 | ME9 |
|---|---|---|---|---|---|---|---|---|---|---|
| 1 | leflunomide | 2 | 2 | 2 | 2 | 2 | 2 | 2 | 2 | 2 |
| 2 | Capryol ® 90 | 6 | 10 | 14 | 6 | 10 | 14 | 6 | 10 | 14 |
| 3 | Tween ® 20 | 22 | 27 | 30 | — | — | — | 6 | 7.5 | 10 |
| 4 | Kolliphor ® RH 40 | — | — | — | 22 | 27 | 30 | 6 | 7.5 | 10 |
| 5 | PEG 400 | 10 | 13 | 16 | 10 | 13 | 16 | 12 | 15 | 18 |
| 6 | water q.s. | 100 | 100 | 100 | 100 | 100 | 100 | 100 | 100 | 100 |
| | Globule Size (nm) | 212.6 ± 2.6 | 150.6 ± 1.8 | 110.3 ± 5.4 | 219.6 ± 6.3 | 140.3 ± 2.9 | 123.3 ± 4.3 | 109.8 ± 7.5 | 70.6 ± 3.5 | 48.3 ± 2.9 |
| | PDI | 0.35 ± 0.09 | 0.42 ± 0.06 | 0.46 ± 0.02 | 0.33 ± 0.05 | 0.43 ± 0.09 | 0.47 ± 0.03 | 0.42 ± 0.08 | 0.31 ± 0.01 | 0.47 ± 0.05 |
| | pH | 5.3 | 5.6 | 5.8 | 5.1 | 5.4 | 5.8 | 5.4 | 5.7 | 5.9 |
| | Assay (%) | 99.24 ± 0.59 | 98.75 ± 1.2 | 98.11 ± 0.36 | 99.03 ± 0.19 | 99.75 ± 0.53 | 99.82 ± 0.34 | 98.62 ± 0.95 | 98.21 ± 0.44 | 98.93 ± 0.91 |

TABLE 2b

Formulation composition and characterization of batches ME10 to ME18 of microemulsion

| SN | Composition (w/v %) | ME10 | ME11 | ME12 | ME13 | ME14 | ME15 | ME16 | ME17 | ME18 |
|---|---|---|---|---|---|---|---|---|---|---|
| 1 | leflunomide | 2 | 2 | 2 | 2 | 2 | 2 | 2 | 2 | 2 |
| 2 | Capmul ® PG2L | 6 | 10 | 14 | 6 | 10 | 14 | 6 | 10 | 14 |
| 3 | Tween ® 20 | 22 | 27 | 30 | — | — | — | 6 | 7.5 | 10 |
| 4 | Kolliphor ® RH 40 | — | — | — | 22 | 27 | 30 | 6 | 7.5 | 10 |
| 5 | PEG 400 | 10 | 13 | 16 | 10 | 13 | 16 | 12 | 15 | 18 |
| 6 | water q.s. | 100 | 100 | 100 | 100 | 100 | 100 | 100 | 100 | 100 |
| | Globule Size (nm) | 267.6 ± 1.6 | 180.6 ± 6.2 | 168.3 ± 1.3 | 192.3 ± 4.1 | 125.4 ± 5.2 | 97.3 ± 2.6 | 118.6 ± 7.1 | 61.5 ± 2.4 | 45.8 ± 3.9 |
| | PDI | 0.36 ± 0.03 | 0.32 ± 0.06 | 0.35 ± 0.02 | 0.33 ± 0.09 | 0.41 ± 0.01 | 0.37 ± 0.08 | 0.46 ± 0.05 | 0.45 ± 0.03 | 0.45 ± 0.06 |
| | pH | 5.2 | 5.4 | 5.5 | 5.4 | 5.7 | 5.9 | 5.3 | 5.9 | 5.9 |
| | Assay (%) | 99.56 ± 0.28 | 99.13 ± 0.65 | 99.87 ± 0.72 | 99.12 ± 64 | 98.84 ± 1.03 | 98.23 ± 0.59 | 98.36 ± 0.31 | 99.06 ± 0.42 | 99.26 ± 0.76 |

Manufacturing Process of Leflunomide Microemulsion Composition

The microemulsion was prepared by adding leflunomide to Capmul® PG 2 L, Tween® 20, Kolliphor® RH 40 and PEG 400. This was mixed properly through vortexing such that leflunomide is completely dissolved. Water was added to this to form a microemulsion. The microemulsion was characterized for particle size, polydispersity index, pH and assay.

Characterization of Microemulsion:

Globule Size: The average globule size, polydispersity index, and zeta potential of the microemulsions were measured using Zetasizer Nano-ZS90 (Malvern Instruments, UK). Briefly, formulated microemulsion was diluted ten times with Milli-Q® water and gently mixed. Particle size and zeta potential were determined at 25° C.

Determination of pH: The pH of the microemulsion formulations was measured using the digital pH meter. Approximate amount of microemulsion was diluted with double-distilled water, and the pH of the diluted mixture was measured under ambient temperature.

Assay: Leflunomide content in the drug loaded microemulsion was estimated in triplicate using HPLC method. One milliliter of microemulsion was dissolved in methanol and appropriately diluted with methanol in a volumetric flask. The peak area of the resultant solution was analyzed at 260 nm.

Example 3-Leflunomide Emulgel Compositions According to the Invention

TABLE 3a

Formulation composition and characterization of batches MEG1 to MEG9 of emulgel

| Composition (w/v %) | | MEG1 | MEG2 | MEG3 | MEG4 | MEG5 | MEG6 | MEG7 | MEG8 | MEG9 |
|---|---|---|---|---|---|---|---|---|---|---|
| 1 | leflunomide | 1 | 1 | 1 | 1 | 1 | 1 | 1 | 1 | 1 |
| 2 | Capryol® 90 | 3 | 5 | 7 | 3 | 5 | 7 | 3 | 5 | 7 |
| 3 | Tween® 20 | 11 | 13.5 | 15 | — | — | — | 3 | 3.75 | 5 |
| 4 | Kolliphor® RH 40 | — | — | — | 11 | 13.5 | 15 | 3 | 3.75 | 5 |
| 5 | PEG 400 | 5 | 6.5 | 8 | 5 | 6.5 | 8 | 6 | 7.5 | 9 |
| 6 | Carbopol® 974 P | 2 | 2.5 | 3 | 2 | 2.5 | 3 | 2 | 2.5 | 3 |
| 7 | water q.s | 100 | 100 | 100 | 100 | 100 | 100 | 100 | 100 | 100 |
| | Globule Size (nm) | 251.6 ± 6.1 | 184.8 ± 2.8 | 157.6 ± 1.6 | 268.3 ± 3.9 | 176.6 ± 5.2 | 144.8 ± 3.6 | 122.6 ± 2.4 | 85.9 ± 4.3 | 68.3 ± 1.8 |
| | PDI | 0.43 ± 0.08 | 0.51 ± 0.02 | 0.49 ± 0.05 | 0.37 ± 0.03 | 0.4 ± 0.01 | 0.42 ± 0.06 | 0.49 ± 0.0 | 0.41 ± 0.05 | 0.43 ± 0.03 |
| | pH | 6.3 | 6.5 | 6.4 | 6.2 | 6.8 | 6.4 | 6.5 | 6.2 | 6.4 |
| | Assay (%) | 99.33 ± 0.94 | 99.81 ± 0.36 | 98.68 ± 0.51 | 99.24 ± 0.21 | 99.63 ± 0.13 | 98.71 ± 0.72 | 99.45 ± 0.36 | 99.71 ± 0.24 | 98.21 ± 0.33 |

TABLE 3b

Formulation composition and characterization of batches MEG10 to MEG18 of emulgel

| Composition (w/v %) | | MEG10 | MEG11 | MEG12 | MEG13 | MEG14 | MEG15 | MEG16 | MEG17 | MEG18 |
|---|---|---|---|---|---|---|---|---|---|---|
| 1 | leflunomide | 1 | 1 | 1 | 1 | 1 | 1 | 1 | 1 | 1 |
| 2 | Capmul® PG2L | 3 | 5 | 7 | 3 | 5 | 7 | 3 | 5 | 7 |
| 3 | Tween® 20 | 11 | 13.5 | 15 | — | — | — | 3 | 3.75 | 5 |
| 4 | Kolliphor® RH 40 | — | — | — | 11 | 13.5 | 15 | 3 | 3.75 | 5 |
| 5 | PEG 400 | 5 | 6.5 | 8 | 5 | 6.5 | 8 | 6 | 7.5 | 9 |
| 6 | Carbopol® 974 P | 2 | 2.5 | 3 | 2 | 2.5 | 3 | 2 | 2.5 | 3 |
| 7 | water q.s | 100 | 100 | 100 | 100 | 100 | 100 | 100 | 100 | 100 |
| | Globule Size (nm) | 310.8 ± 2.6 | 247.6 ± 3.8 | 189.9 ± 2.4 | 244.6 ± 77.2 | 149.3 ± 2.5 | 133.6 ± 3.6 | 142.3 ± 3.1 | 75.6 ± 4.5 | 60.3 ± 3.4 |
| | PDI | 0.46 ± 0.04 | 0.38 ± 0.07 | 0.39 ± 0.01 | 0.41 ± 0.06 | 0.43 ± .05 | 0.43 ± 0.03 | 0.53 ± 0.07 | 0.46 ± 0.03 | 0.49 ± 0.04 |
| | pH | 6.3 | 6.7 | 6.5 | 6.6 | 6.4 | 6.8 | 6.6 | 6.3 | 6.4 |
| | Assay (%) | 99.6 ± 0.11 | 98.54 ± 0.87 | 99.41 ± 0.32 | 98.59 ± 0.58 | 98.69 ± 0.91 | 99.21 ± 0.22 | 98.49 ± 0.72 | 99.19 ± 0.16 | 98.06 ± 0.89 |

Manufacturing Process for Preparation of Emulgel Composition According to the Invention Carbopol® 974 P was dispersed in water to swell and form a gel base. pH was adjusted using triethanolamine.

Microemulsion formed in batches ME1 to ME18 was added to the gel base to form microemulgel.

The compositions were characterized for particle size, polydispersity index, pH and assay.

Characterization of Microemulgel:
1. Globule size of microemulgel: Globule size was estimated by diluting (ten times) a defined quantity of the gel using Milli-Q® water and analyzed.
2. Viscosity of microemulgel: The viscosity of the leflunomide microemulgel was determined using a Brookfield digital viscometer DVE, with spindle S94 (T-shaped spindle) rotated at 2 rpm for a sample of 50 grams.
3. Spreadability: The spreadability of the optimized gels was measured by the weighting of 0.5 g of gel and spreading it on a circle of 2 cm diameter pre-marked on a glass plate and then another glass plate was applied. A 500 g weight was kept on the upper glass plate for 5 min. The circle-diameter of the spreading gel was measured using the following formula.

% spread by area=$A2/A1 \times 100$

Where A1=diameter of initial circle (2 cm), and A2=diameter of circle after spreading.

4. In-vitro release Studies: In-vitro drug release studies were performed using Phoenix DB-6 Diffusion Tester using SUPOR 0.45 µm, 25 mm membrane. The gel weighing 0.25 g was taken in the donor compartment. The receptor compartment contained 15 ml phosphate buffer solution pH 7.4: methanol at 60:40 ratio as a diffusion medium. The temperature of the buffer was maintained at 32° C. and it was stirred using a magnetic bead at a rate of 800 rpm. At a predefined time intervals 0.5 ml aliquot of the sample was taken for analysis and equal amount was replaced with fresh diffusion media. Samples were analyzed for both the parent and the metabolite using a validated HPLC method and drug concentrations were quantified.

Select compositions from above with the desired characterization were further analyzed for viscosity, spreadability and in-vitro release studies.

TABLE 4

Formulation composition and characterization data for selected batches of microemulgel

| SN | Composition (w/v %) | MEG 2 | MEG 5 | MEG 8 | MEG 11 | MEG 14 | MEG 17 |
|---|---|---|---|---|---|---|---|
| 1 | leflunomide | 1 | 1 | 1 | 1 | 1 | 1 |
| 2 | Capryol ® 90 | 5 | 5 | 5 | — | — | — |
| 3 | Capmul ® PG2L | — | — | — | 5 | 5 | 5 |
| 4 | Tween ® 20 | 13.5 | — | 3.75 | 13.5 | — | 3.75 |
| 5 | Kolliphor ® RH 40 | — | 13.5 | 3.75 | — | 13.5 | 3.75 |
| 6 | PEG 400 | 6.5 | 6.5 | 7.5 | 6.5 | 6.5 | 7.5 |
| 7 | Carbopol ® 974 P | 2.5 | 2.5 | 2.5 | 2.5 | 2.5 | 2.5 |
| 8 | water q.s. | 100 | 100 | 100 | 100 | 100 | 100 |
|  | Viscosity (cP) | 136598 ± 136 | 145216 ± 221 | 115149 ± 103 | 141229 ± 169 | 149269 ± 221 | 121639 ± 162 |
|  | Spreadability (%) | 43.6 | 37.9 | 44.3 | 39.6 | 32.8 | 42.1 |

Based on the various characterization results and the release studies, MEG8 and MEG17 were kept for stability studies at 25° C.±2° C./60% RH±5% and was further evaluated for in-vitro permeation studies.

TABLE 5

In-vitro release studies of MEG8 and MEG17 batches

| SN | Composition (% w/v) | MEG8 | | MEG17 | |
|---|---|---|---|---|---|
| 1 | leflunomide | 0.5 | 1 | 0.5 | 1 |
| 2 | Capryol ® 90 | 5 | 5 | — | — |
| 3 | Capmul ® PG2L | — | — | 5 | 5 |
| 4 | Tween ® 20 | 3.75 | 3.75 | 3.75 | 3.75 |
| 5 | Kolliphor ® RH 40 | 3.75 | 3.75 | 3.75 | 3.75 |
| 6 | PEG 400 | 7.5 | 7.5 | 7.5 | 7.5 |
| 7 | Carbopol ® 974 P | 2.5 | 2.5 | 2.5 | 2.5 |
| 8 | water q.s | 100 | 100 | 100 | 100 |
|  | Globule Size (nm) | 81.36 ± 1.6 | 85.9 ± 4.3 | 74.39 ± 3.6 | 75.6 ± 4.5 |
|  | PDI | 0.423 ± 0.03 | 0.41 ± 0.05 | 0.432 ± 0.06 | 0.46 ± 0.03 |
|  | Cumulative amount released/area (mcg/sq. cm) in 8 hours | 523 ± 3.2 | 1070 ± 2.47 | 532 ± 1 | 1100 ± 2.1 |
|  | Flux (mcg/sq. cm/hr) | 79.5 | 177 | 79 | 180 |

TABLE 6

One month stability studies of MEG8 and MEG17 batches

| Formulation | Duration | Particle Size (nm) | PDI | Assay (%) | Viscosity (cP) |
|---|---|---|---|---|---|
| 25° C. ± 2° C./60% RH ± 5% | | | | | |
| MEG8 | Initial (day 1) | 85.9 ± 2.3 | 0.41 ± 0.03 | 99.71 ± 0.25 | 115149 ± 103 |
|  | 1 month | 89.2 ± 3.6 | 0.38 ± 0.08 | 99.07 ± 0.46 | 109875 ± 129 |
| MEG17 | Initial (day 1) | 75.6 ± 1.6 | 0.46 ± 0.07 | 99.19 ± 0.53 | 121639 ± 162 |
|  | 1 month | 81.5 ± 3.9 | 0.39 ± 0.04 | 98.69 ± 0.79 | 115698 ± 201 |
| 40° C. ± 2° C./75% RH ± 5%. | | | | | |
| MEG8 | Initial (day 1) | 85.9 ± 2.3 | 0.41 ± 0.03 | 99.71 ± 0.25 | 115149 ± 103 |
|  | 1 month | 90.8 ± 2.8 | 0.45 ± 0.06 | 99.13 ± 0.21 | 107156 ± 109 |
| MEG17 | Initial (day 1) | 75.6 ± 1.6 | 0.46 ± 0.07 | 99.19 ± 0.53 | 121639 ± 162 |
|  | 1 month | 84.3 ± 4.3 | 0.43 ± 0.02 | 98.54 ± 0.16 | 113126 ± 157 |

The formulations MEG8 and MEG17 were further evaluated for in-vitro permeation studies using human cadaver skin as follows:

TABLE 7

Parameters for In-vitro permeation studies

| Parameters | Details |
|---|---|
| Diffusion apparatus | Phoenix DB-6 Diffusion Tester |
| Diffusion Membrane | Human cadaver skin (viable) |
| Diffusion medium and volume | pH 7.4 phosphate buffer:Methanol (50:50% v/v), 10 ml |
| Temperature | 32° C. ± 0.5° C. |
| RPM | 800 |
| Intervals | 0, 0.5, 1, 2, 3, 4, 5, 6, 8 and 24 hours |
| Sampling and dilution method | A 0.5 ml aliquot was removed from each vessel at given time point |
| Analysis | Sample was analyzed using HPLC at $\lambda_{max}$ 260 nm (leflunomide) & 290 nm (teriflunomide) |

TABLE 8a

In vitro permeation studies for formulation MEG8

|  | MEG 8 0.5% (Dose: 1.25 mg) | | MEG 8 1% (Dose: 2.5 mg) | |
|---|---|---|---|---|
|  | leflunomide | teriflunomide | leflunomide | teriflunomide |
| Cumulative Amount permeated (mcg/sq. cm in 24 hours) | 2.6 ± 0.2 | 2.9 ± 0.087 | 8.7 ± 0.55 | 10.58 ± 1.17 |
| Flux (mcg/cm2/h) | 0.11 | 0.12 | 0.36 | 0.44 |

TABLE 8b

In vitro permeation studies for formulation MEG17

|  | MEG 17 0.5% | | MEG 17 1% | |
|---|---|---|---|---|
|  | leflunomide | teriflunomide | leflunomide | teriflunomide |
| Cumulative Amount permeated (mcg/sq. cm in 24 hours) | 1.2 ± 0.047 | 0.55 ± 0.09 | 15.2 ± 0.078 | 20.4 ± 0.19 |
| Flux (mcg/cm2/h) | 0.05 | 0.02 | 0.63 | 0.85 |

In all formulations tested, viz. MEG 17 0.5%, MEG 17 1%, MEG 8 0.5% and MEG 8 1%, it was observed that both the prodrug-leflunomide and the active metabolite-teriflunomide permeated through skin membrane.

One of the key evaluations for the topical drug formulations is to assess the irritation potential of the drug being tested along with the excipients. Often the inactive ingredients e.g. oils, surfactants, co-surfactants can be irritants to the skin. Therefore it is critically important to use the right excipients which are non-irritating and in the permissible concentrations. With an objective to assess the irritation potential of the drug and the excipient(s) added in this present emulgel formulation, we performed acute dermal skin irritation studies using the emulgel with and without leflunomide.

Test animal(s): Rabbit
Species/strain used: New Zealand White Rabbit
Number of animal(s) used of each sex: 6 Males

TABLE 9

Details of animals used for dermal irritation potential studies of MEG8 & MEG17 batches

| Animal Code | Treatment groups | Rabbit weight (gm) Start of the experiment | Rabbit weight (gm) end of the experiment |
|---|---|---|---|
| RV1 | Vehicle | 1700 | 1950 |
| RH1 | Microemulsion-based gel containing 1% leflunomide | 1650 | 1865 |
| RV2 | Vehicle | 1600 | 1970 |
| RV3 | Vehicle | 1500 | 1740 |
| RH2 | Microemulsion-based gel containing 1% leflunomide | 1620 | 1850 |
| RH3 | Microemulsion-based gel containing 1% leflunomide | 1510 | 1740 |

RV1, RH1, RV2,
$ RV: Animal receiving Vehicle as treatment ('R' indicates Rabbit and 'V' indicates Vehicle).
$$ RH: Animal receiving Microemulsion-based gel with 1% leflunomide as a treatment ('R' indicates Rabbit and 'H' indicates High dose formulation i.e. Microemulsion-based gel containing 1% leflunomide)

The dermal irritation potential was conducted as follows—
Source of animal(s): National Institute of Bio Sciences, 14, Ajay Apartment, Manikbaug, Opp: Shivsagar-II, Sinhgad Road, Pune, India.
Housing conditions: Temperature-21±1° C.; Relative Humidity-30 to 70%
Diet: Standard rabbit diet purchased from National Institute of Bio Sciences, Pune, India.
The hair were shaved with a hair clipper
Details of patch materials used and patching technique: Cotton gauze with a nonirritating tape.
Details of test chemical preparation, application, and removal: The test chemical was applied to a small area (approximately 6 cm$^2$) of skin and covered with a surgical cotton gauze, which was held in place with non-irritating tape. A dose of 0.5 gm of the gel was applied onto approximately 6 cm$^2$ area of the shaved dorsal side of rabbits.

Discussion

One animal was used per group. No erythema, eschar formation, and edema were observed post 3 minutes and 1-hour application, in Group 1 (Microemulsion-based gel with 1% leflunomide) as well as in Group 3 (Vehicle group: Microemulsion-based gel without leflunomide). The observations indicated that microemulsion-based gel with 1% leflunomide exposure can be allowed to stay on the skin surface up to four hours. No erythema, eschar formation, and edema were observed until 4-hours, and were observed up to 24 hours and thereafter for any signs and symptoms of clinically relevant abnormality. The average score for erythema, eschar formation, and edema for all the time intervals for Group 1 and Group 3 were reported to be zero. The microemulsion-based gel with 1% leflunomide and vehicle i.e. microemulsion-based gel without leflunomide showed no irritation potential in acute dermal irritation study.

Leflunomide is a pro-drug. Leflunomide is an isoxazole, which is metabolized into an active metabolite melononitrilamide i.e. A771726, it is also called teriflunomide. This metabolite is pharmacologically active and is responsible to exert the desired DHODH inhibition activity a rate limiting enzyme of the de novo pyrimidine synthesis pathway. In the plasma leflunomide is not detected and in the clinical studies teriflunomide was quantified as pharmacologically active component.

The formulations MEG8 and MEG17 were further evaluated for pharmacokinetic parameters as follows.
Test animal(s): Wistar Rats of 160-200 gms
Number of animal(s) used of each sex: 33 Males (6 for pilot study and 27 for main study)
Source of animal(s): National Institute of Bio Sciences, 14, Ajay Apartment, Manikbaug, Opp: Shivsagar-II, Sinhgad Road.
Diet: Standard Rabbit Diet Purchased from National Institute of Bio Sciences, Pune.

A dose of MEG 17 [0.5%] was applied onto 6 cm$^2$ area of the shaved dorsal side of the Wistar rats. The formulation was kept in contact with the skin for 4 hours with the help of adhesive tape. Upon removal of the covering, the applied surface was wiped off with alcohol swabs to remove the unabsorbed drug formulation remaining on the skin if any.

Pilot study: Six animals were dosed topically with Microemulsion based gel with 0.5% leflunomide. The blood samples were withdrawn at 0.5, 1, 1.5, 2, 4, 6, 9, 12, 24, 36 hrs time intervals into heparinized tubes and were processed for analysis. Table 10 illustrates animal-wise blood collection schedule for pilot study.

TABLE 10

Blood collection schedule for Pilot study (0.5 ml at each time point)

| Time Points in Hrs | R1 | R2 | R3 | R4 | R5 | R6 |
|---|---|---|---|---|---|---|
| 0.5 | ✓ | ✓ | | | | |
| 1 | | | ✓ | ✓ | | |
| 1.5 | | | | | ✓ | ✓ |
| 2 | ✓✓ | ✓✓ | | | | |
| 4 | | | ✓✓ | ✓✓ | | |
| 6 | | | | | ✓✓ | ✓✓ |
| 9 | ✓ | ✓ | | | | |
| 12 | | | ✓ | ✓ | | |
| 24 | ✓✓ | ✓✓ | | | ✓ | ✓ |
| 36 | | | ✓✓ | ✓✓ | ✓✓ | ✓✓ |

✓: Right Eye, ✓✓: Left Eye, per time point min. 2 samples were there

Main Study: Upon successful validation of the bioanalytical method by pilot study, main study was undertaken. Table 11 illustrates the group-wise distribution of the animals in main study. It was conducted in two phases. Phase 1 was held on Days 1 and 2; 3 animals from each group dosed in this phase. Phase 2 was held on days 6 and 7; 6 animals from each group dosed in this phase. The blood samples were withdrawn at 0.5, 1, 1.5, 2, 4, 6, 9, 12, 24, 36 hrs time intervals into heparinized tubes and were sent for the analysis. Table 12 illustrates animal-wise blood collection schedule for main study for one group. The same scheme was followed for all the three groups of animals.

TABLE 11

Group-wise distribution of the animals for Main Study

| Group | Group 1: Microemulsion based gel with 0.5% MEG17 | Group 2: Microemulsion based gel with 1% MEG17 | Group 3: Oral Suspension of the equivalent dose (5 mg) | Total |
|---|---|---|---|---|
| No. of animals per group | 9 | 9 | 9 | 27 |

TABLE 12

Blood collection schedule for Main study for each group consisting of 9 animals (0.5 ml at each time point)

| Time Points in hours | R1 | R2 | R3 | R4 | R5 | R6 | R7 | R8 | R9 |
|---|---|---|---|---|---|---|---|---|---|
| 0.5 | ✓ | ✓ | ✓ | | | | | | |
| 1 | | | | ✓ | ✓ | ✓ | | | |
| 1.5 | | | | | | | ✓ | ✓ | ✓ |
| 2 | ✓✓ | ✓✓ | ✓✓ | | | | | | |
| 4 | | | | ✓✓ | ✓✓ | ✓✓ | | | |
| 6 | | | | | | | ✓✓ | ✓✓ | ✓✓ |
| 9 | ✓ | ✓ | ✓ | | | | | | |
| 12 | | | | ✓ | ✓ | ✓ | | | |
| 24 | | | | ✓✓ | ✓✓ | ✓✓ | ✓ | ✓ | ✓ |
| 36 | ✓✓ | ✓✓ | ✓✓ | | | | ✓✓ | ✓✓ | ✓✓ |

✓: Right Eye, ✓✓: Left Eye; per time point min. 3 samples were there

The blood samples obtained from the study samples were subjected to HPLC analysis using the method developed for bioanalysis of teriflunomide from rat plasma.

Figure 1A:
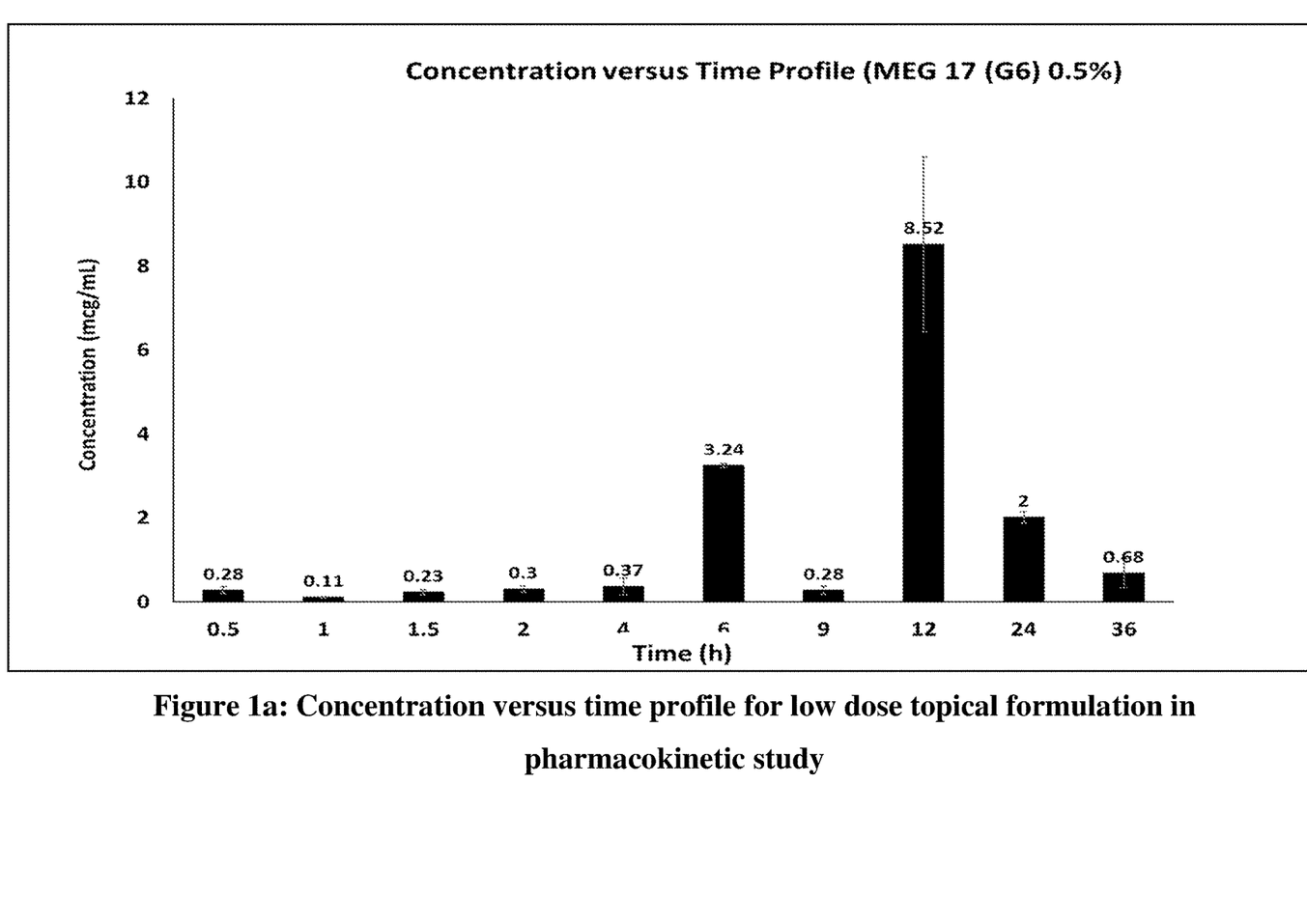
FIG. 1a: Concentration versus time profile for low dose topical formulation in pharmacokinetic study.
Figure 1B:
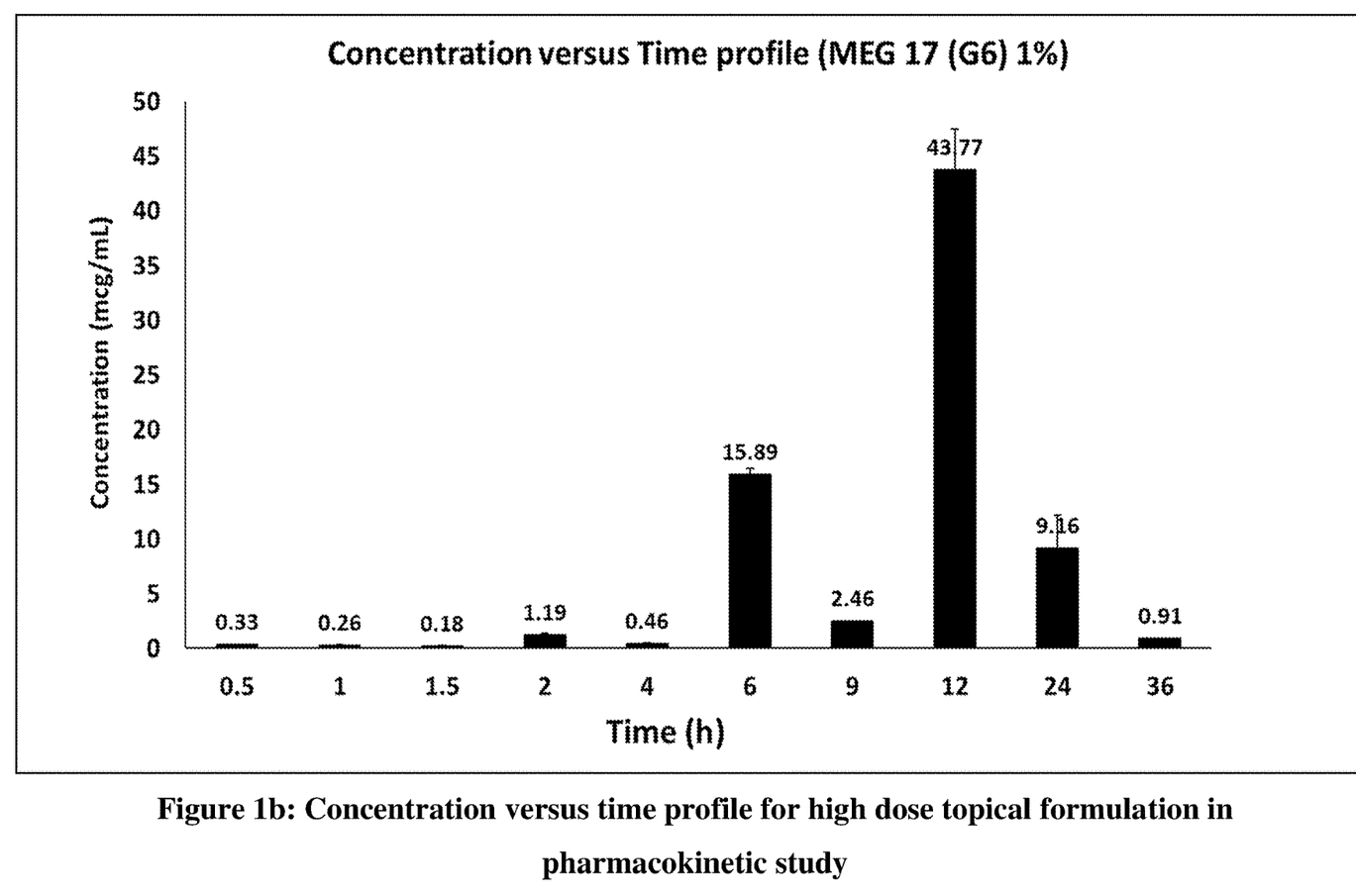
FIG. 1b: Concentration versus time profile for high dose topical formulation in pharmacokinetic study.

Discussion: After application of the topical gel containing 1% (high dose) & 0.5% (low dose) of leflunomide, teriflunomide was first detected in plasma at 0.5 h in all three studies and its concentration increased steadily up to 12 h (FIG. 1a & FIG. 1b).

Figure 1C:
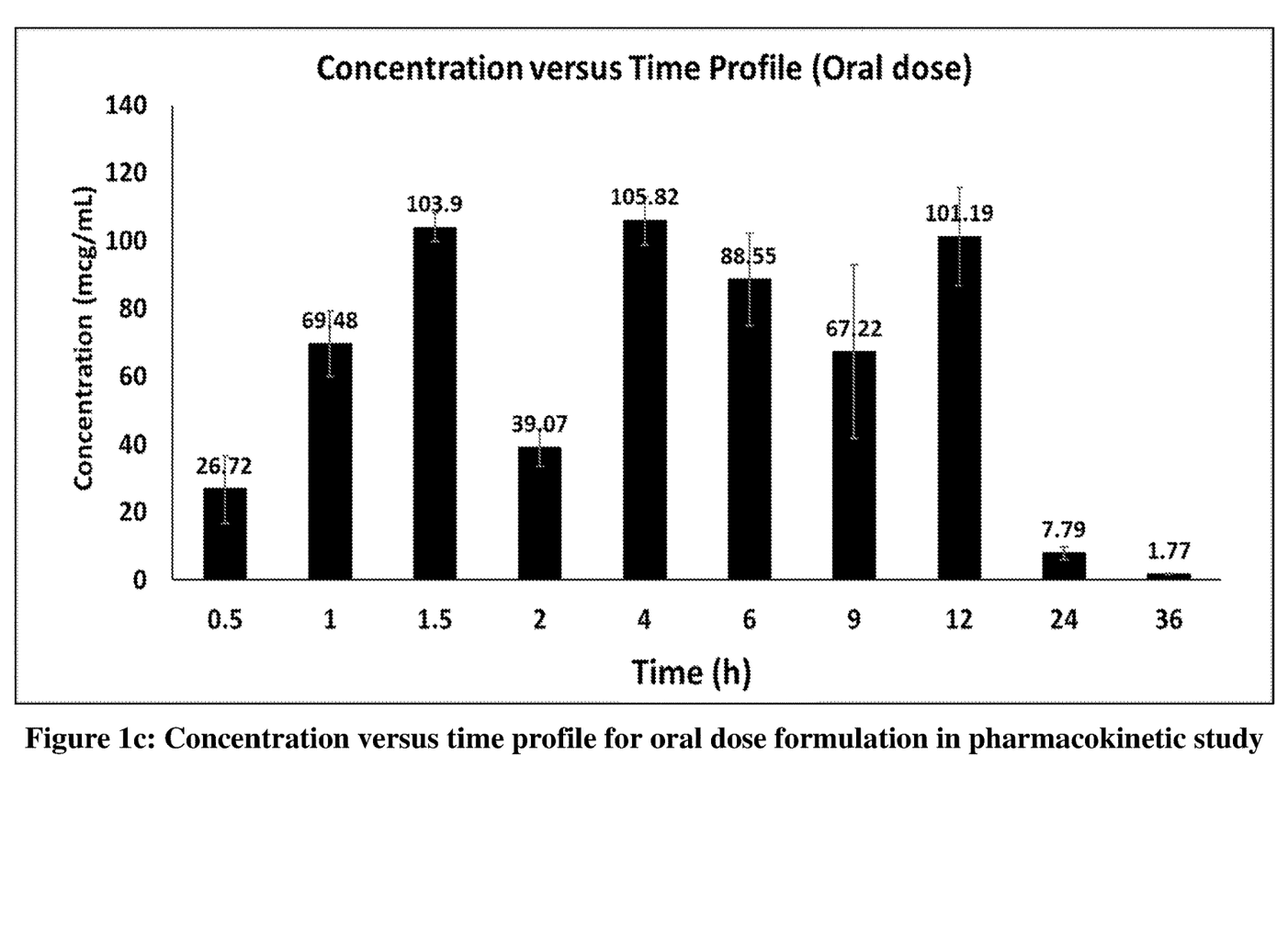
FIG. 1c: Concentration versus time profile for oral dose formulation in pharmacokinetic study.

In case of oral administration, the concentration increased steadily up to 4 h with a minor drop at 6 h and 9 h, it again increased at 12 h and thereafter decreased steadily (FIG. 1c).

Table 13 shows the Pharmacokinetic parameters calculated on the basis of results obtained for pharmacokinetic studies.

TABLE 13

Pharmacokinetic parameters of the study conducted

| Pharmacokinetic Parameter | MEG 17 (G6) 1% (Dose: 5 mg) | MEG 17 (G6) 0.5% (Dose: 2.5 mg) | Oral dose formulation (Dose: 5 mg) |
|---|---|---|---|
| $C_{max}$ (mcg/mL)* | 42.47 ± 1.83 | 8.52 ± 2.08 | 105.9 ± 7.1 |
| $T_{max}$ (h)* | 12 ± 0.0 | 12 ± 0.0 | 4 ± 0.0 |
| $AUC_{0-36}$ (mcg · h/mL) | 416.39 | 86.26 | 1589.38 |

*Statistically significant; Mean ± S.D., n = 3

Figure 2:
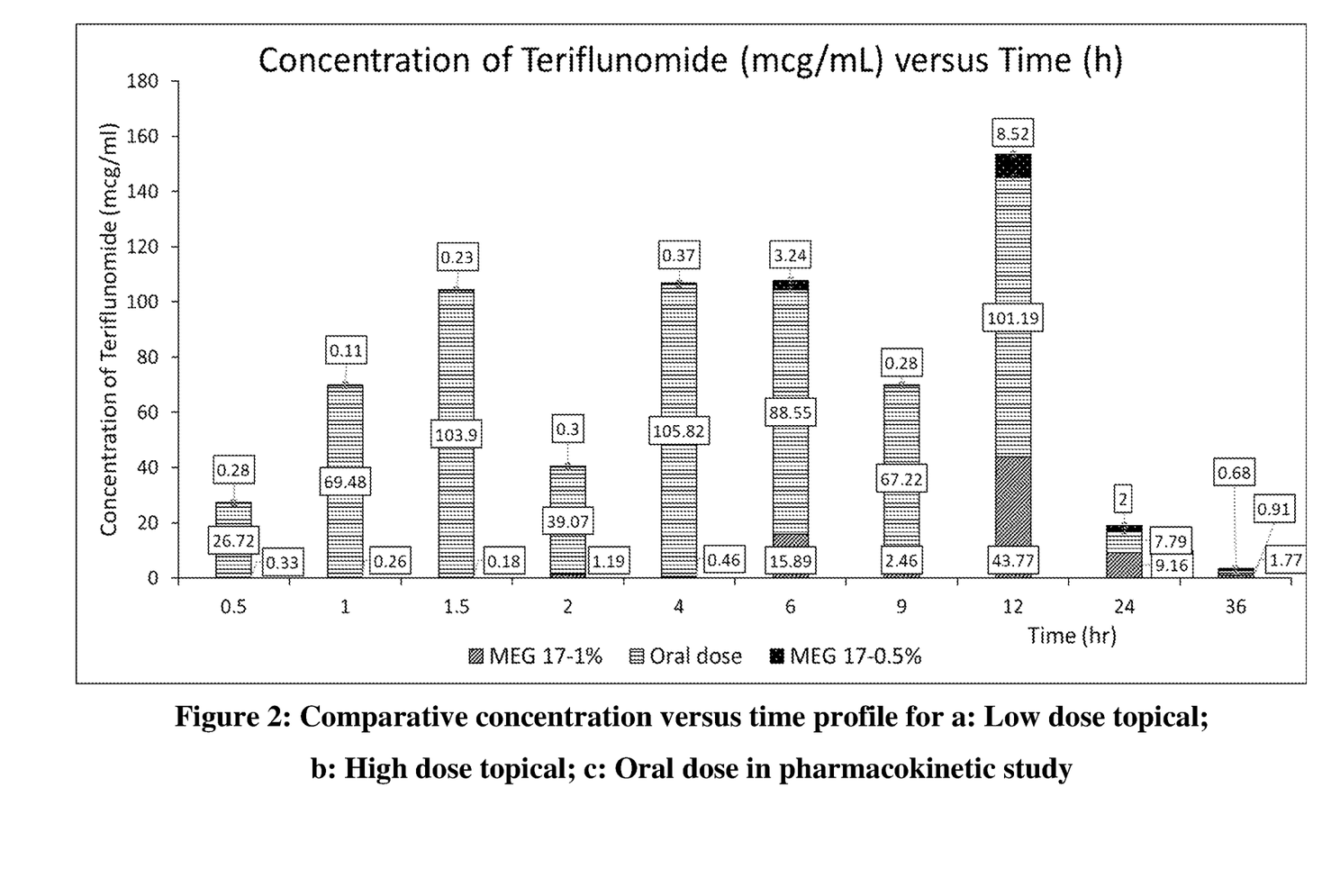
FIG. 2 Comparative concentration versus time profile for a: Low dose topical; b: High dose topical; c: Oral dose in pharmacokinetic study.

FIG. 2 shows a comparative concentration versus time profile for all three studies.

For determination of pharmacokinetic profile of topical formulations, it is advisable to generate the dermatokinetic profile by measuring the concentration of the drug in synovial fluid along with detection of plasma concentration levels; however, plasma concentration versus time profile alone cannot give a better understanding of the dermatokinetic profile of the topical formulation.

The formulations described herein may comprise the listed ingredients, or consist essentially of the listed ingredients, or consist of the listed ingredients. By consisting essentially of the listed ingredients it is understood that the novel and basic properties of the formulation are primarily the solubility and absorption through the skin. The formulations described herein may comprise the listed ingredients in the listed amounts, or consist essentially of the listed ingredients in the listed amounts, or consist of the listed ingredients in the listed amounts.

What is claimed is:

1. A topical microemulsion-based emulgel composition comprising:
   a. 0.5-1.0 (% w/v) leflunomide;
   b. 5 (% w/v) propylene glycol monocaprylate;
   c. 3.75 (% w/v) polysorbate 20;
   d. 3.75 (% w/v) polyoxyl 40 hydrogenated castor oil;
   e. 7.5 (% w/v) polyethylene glycol 400;
   f. 2.5 (% w/v) carbomer; and
   g. q.s. water.

2. The topical microemulsion-based emulgel composition of claim 1, wherein the composition consists of:
   a. 1.0 (% w/v) leflunomide;
   b. 5 (% w/v) propylene glycol monocaprylate;
   c. 3.75 (% w/v) polysorbate 20;
   d. 3.75 (% w/v) polyoxyl 40 hydrogenated castor oil;
   e. 7.5 (% w/v) polyethylene glycol 400;
   f. 2.5 (% w/v) carbomer; and
   g. q.s. water.

3. A topical microemulsion-based emulgel composition comprising:
   a. 0.5-1.0 (% w/v) leflunomide;
   b. 5 (% w/v) propylene glycol dilaurate;
   c. 3.75 (% w/v) polysorbate 20;
   d. 3.75 (% w/v) polyoxyl 40 hydrogenated castor oil;
   e. 7.5 (% w/v) polyethylene glycol 400;
   f. 2.5 (% w/v) carbomer; and
   g. q.s. water.

4. The topical microemulsion-based emulgel composition of claim 3, wherein the composition consists of:
   a. 1.0 (% w/v) leflunomide;
   b. 5 (% w/v) propylene glycol dilaurate;

c. 3.75 (% w/v) polysorbate 20;
d. 3.75 (% w/v) polyoxyl 40 hydrogenated castor oil;
e. 7.5 (% w/v) polyethylene glycol 400;
f. 2.5 (% w/v) carbomer; and
g. q.s. water.

* * * * *